United States Patent [19]

Laval et al.

[11] Patent Number: 4,647,642

[45] Date of Patent: Mar. 3, 1987

[54] PROCESS FOR THE PREPARATION OF POLYPHENOL DERIVATIVES AND DERMATIVES OBTAINED THEREBY

[75] Inventors: François Laval, Champs sur Marne; Pierre J. Madec, Orleans; Ernest Marechal, Paris, all of France

[73] Assignee: Commissariat a l'Energie Atomique, Paris, France

[21] Appl. No.: 707,534

[22] Filed: Mar. 4, 1985

Related U.S. Application Data

[63] Continuation of Ser. No. 471,537, Mar. 2, 1983, abandoned.

[30] Foreign Application Priority Data

Mar. 3, 1982 [FR] France ................. 82 03522

[51] Int. Cl.$^4$ ............................................. C08G 77/04
[52] U.S. Cl. ..................... 528/25; 525/464; 525/474; 525/479; 528/15; 528/29; 528/31
[58] Field of Search ............ 528/25, 29, 31, 15; 525/479, 474, 464

[56] References Cited

U.S. PATENT DOCUMENTS 4,042,566 8/1977 Murphy ............................. 526/273
4,166,078 8/1979 Getson ............................... 528/25

FOREIGN PATENT DOCUMENTS 0022073 1/1981 European Pat. Off. .
2080272 11/1971 France .
2483441 12/1981 France .
768748 2/1957 United Kingdom .

Primary Examiner—Melvyn I. Marquis

[57] ABSTRACT

The present invention relates to a process for the preparation of polyphenol derivatives, new derivatives obtained by this process and their use in the preparation of polymers and copolymers.

This process consists of reacting a polyphenol with 1-allyloxy-2,3-epoxypropane of formula:

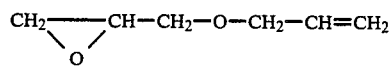

in the presence of a catalyst constituted by a tertiary amine or an alkali hydroxide to obtain a polyphenol derivative having two reactive functions, i.e. allyl and hydroxyl at each end.

Preferably, the phenols used are bisphenol A, bisphenol A derivatives, such as polysulphones or polycarbonates and phenol-formaldehyde resins.

The derivatives obtained in this way having two reactive functions of different types at each end of their chain (hydroxyl and allyl) can participate in polymerization, copolymerization and/or crosslinking reactions.

3 Claims, No Drawings

PROCESS FOR THE PREPARATION OF POLYPHENOL DERIVATIVES AND DERMATIVES OBTAINED THEREBY

This application is a continuation of application Ser. No. 471,537, filed Mar. 2, 1983, and now abandoned.

BACKGROUND OF THE INVENTION

The present invention relates to a process for the preparation of polyphenol derivatives, the derivatives obtained by this process, their use for the preparation of polymers and copolymers, which may be crosslinked, and the copolymers obtained in this way.

More specifically, it relates to the preparation of polyphenol derivatives having at each end at least two reactive functions of different types, constituted respectively by a hydroxyl function and an allyl function.

Such derivatives are of considerable interest in the production of crosslinked or uncrosslinked random, block and graft copolymers and polymers, usable e.g. for producing adhesives, reinforced plastics or members having to withstand high temperatures.

SUMMARY OF THE INVENTION

The present invention relates to a process for the preparation of polyphenol derivatives having at least two reactive functions of different types at each of its ends, wherein it consists of reacting a polyphenol with 1-allyloxy-2,3-epoxypropane of formula:

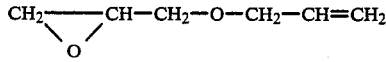

in the presence of a basic catalyst constituted either by a tertiary amine, or by an alkali hydroxide.

Through performing this reaction in the presence of a catalyst constituted by an alkali hydroxide or an amine, it is possible to rapidly and quantitatively change the phenol function into a double function, namely an allyl function and a hydroxyl function.

According to a first embodiment of this process, the polyphenol is of formula:

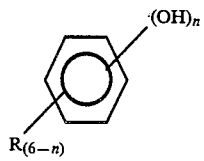

in which R represents a hydrogen atom, a halogen atom, an alkyl radical in $C_1$ to $C_5$ or an alkoxy radical in $C_1$ to $C_5$ and in which n is an integer between 2 and 6.

In the expression $C_1$ to $C_5$ the subscript indicates the number of carbon (C) atoms in the radical. This convention is followed herein.

According to a second embodiment of this process, the polyphenol is in accordance with the formula:

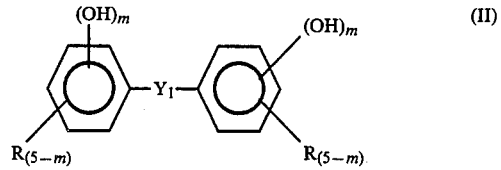

in which R represents a hydrogen atom, a halogen atom, an alkyl radical in $C_1$ to $C_5$ or an alkoxy radical in $C_1$ to $C_5$, $Y_1$ representing

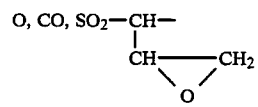

or the group

or $R^1$ and $R^2$, which can be the same or different, stand for hydrogen, a halogen atom, an alkyl radical in $C_1$ to $C_4$, an alkoxy radical in $C_1$ to $C_4$, a cycloalkyl radical of $C_3$ to $C_6$ or the group

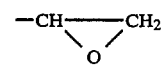

and m is an integer between 1 and 5.

According to a third embodiment of the process according to the invention, the polyphenol is in accordance with the formula:

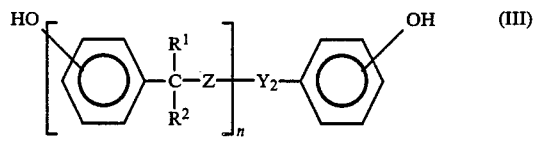

in which $R^1$ and $R^2$, which can be the same or different, represents hydrogen, a halogen atom, an alkyl radical of $C_1$ to $C_4$, an alkoxy radical of $C_1$ to $C_4$, a cyclo alkyl radical of $C_3$ to $C_6$ or the group

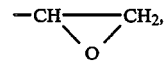

Z represents a single bond or the group

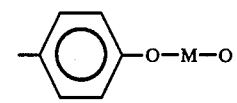

with M representing —CO or

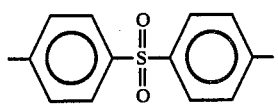

Y₂ represents a single bond, the radical

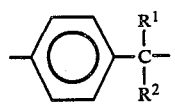

or the radical

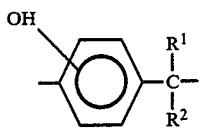

n being an integer equal to or higher than 1.

Preferably, the polyphenol is bisphenol A or a bisphenol A derivative, such as α, ω-diphenol polysulphone or α, ω-diphenol polycarbonate.

According to a fourth embodiment of the process according to the invention, the polyphenol is a phenol-formaldehyde resin of formula:

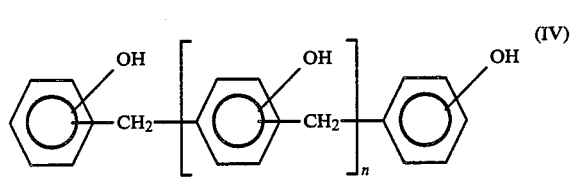

in which n is an integer equal to or higher than 1.

Advantageously, the polyphenol is chosen from the group including polyphenol A, 1,1-bis(4-hydroxyphenylcyclohexane)(bisphenol C), 4,4'-dihydroxybenzophenone, 4,4'-dihydroxydiphenylsulphone, resorcinol, hydroquinone, catechol and phloroglucinol.

Examples of tertiary amines which can be used as the catalyst in the process according to the invention, are dimethyl dodecylamine and triethanolamine.

Preferably, the reaction is performed in the absence of a solvent at an adequate temperature to obtain the solubility of the polyphenol in 1-allyloxy-2,3-epoxypropane and working takes place at a temperature exceeding 80° C., generally at 120° C.

However, this reaction can also be performed in the presence of an inert solvent, such as chlorobenzene or diethylene glycol dimethylether (diglyme).

The invention also relates to novel polyphenol derivatives obtained by the process of the invention.

According to the first mode, these derivatives comply with formula:

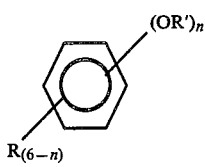

of which R represents a hydrogen atom, a halogen atom, an alkyl radical of $C_1$ to $C_5$ or an alkoxy radical in $C_1$ to $C_5$, whilst n represents an integer between 2 and 6 and R' represents $$-CH_2-CH-CH_2-O-CH_2-CH=CH_2.$$
$$\phantom{-CH_2-}|$$
$$\phantom{-CH_2-}OH$$

According to the second embodiment, these derivatives comply with formula:

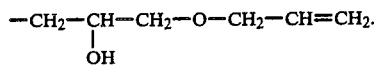

in which R' represents $$-CH_2-CH-CH_2-O-CH_2-CH=CH_2,$$
$$\phantom{-CH_2-}|$$
$$\phantom{-CH_2-}OH$$

R represents a hydrogen atom, a halogen atom, an alkyl radical of $C_1$ to $C_5$ or an alkoxy radical of $C_1$ to $C_5$, $Y_1$ represents O, CO, $SO_2$,

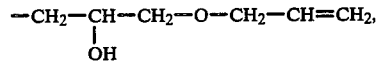

or the group

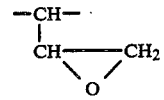

with $R^1$ and $R^2$, which can be the same or different, representing hydrogen, a halogen atom, an alkyl radical in $C_1$ to $C_4$, an alkoxy radical of $C_1$ to $C_4$, a cycloalkyl radical of $C_3$ to $C_6$ or the group

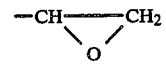

and m is an integer between 1 and 5.

According to a further embodiment, these derivatives comply with the following formula:

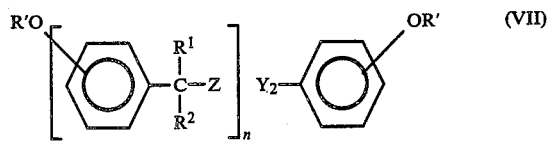

in which R' represents

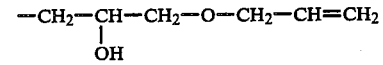

and $R^1$ and $R^2$, which can be the same or different, represent a hydrogen atom, a halogen atom, an alkyl radical of $C_1$ to $C_4$, an alkoxy radical of $C_1$ to $C_4$, a cycloalkyl radical in $C_3$ to $C_6$ or the group

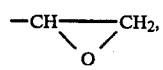

Z stands for a single bond or the group

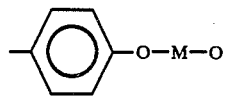  (A)

with M representing CO or

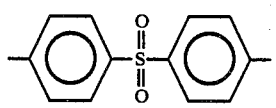  (B)

$Y_2$ represents a single bond, the radical

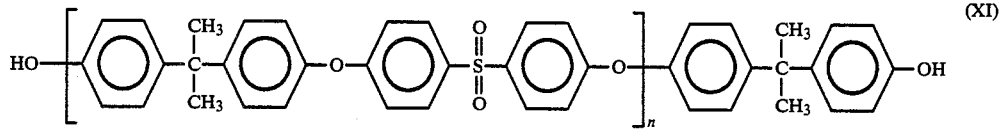

or the radical (D)

and n is an integer equal to or higher than 1.
Examples of such derivatives are the derivative complying with formula:

(VIII)

$$CH_2=CH-CH_2-O-CH_2-\underset{OH}{CH}-CH_2-O-\underset{CH_3}{\overset{CH_3}{C}}-$$

$$-O-CH_2-\underset{OH}{CH}-CH_2-O-CH_2-CH=CH_2$$

which can be prepared by reacting bisphenol A of formula:

(IX)

$$OH-\underset{CH_3}{\overset{CH_3}{C}}-OH$$

with 1-allyloxy-2,3-epoxy propane according to the process of the invention, the derivative complying with the formula:

(X)

$$CH_2=CH-CH_2-O-CH_2-\underset{OH}{CH}-CH_2-O-\left[\underset{CH_3}{\overset{CH_3}{C}}-\right.$$

$$\left.-\underset{}{\overset{O}{\underset{\|}{S}}}-O-\underset{CH_3}{\overset{CH_3}{C}}-\right]_n$$

$$-O-CH_2-\underset{OH}{CH}-CH_2-O-CH_2-CH=CH_2$$

with n being an integer equal to or higher than 1, which can be obtained by reacting a α, ω-diphenol polysulphone of formula:

(XI)

$$HO-\underset{CH_3}{\overset{CH_3}{C}}-O-\underset{}{\overset{O}{\underset{\|}{S}}}-O-\left[\underset{CH_3}{\overset{CH_3}{C}}\right]_n-OH$$

in which n is an integer equal to or higher than 1, with 1-allyloxy-2,3-epoxy propane in the presence of a tertiary amine of an alkali hydroxide, and the derivative complying with formula:

(XII)

$$CH_2=CH-CH_2-O-CH_2-\underset{OH}{CH}-CH_2-O-\left[\underset{CH_3}{\overset{CH_3}{C}}-\right.$$

$$\left.-O-\underset{O}{\overset{\|}{C}}-O-\underset{CH_3}{\overset{CH_3}{C}}-O-CH_2-\right]_n$$

$$-\underset{OH}{CH}-CH_2-O-CH_2-CH=CH_2$$

in which n is an integer equal to or higher than 1, which can be obtained by reacting a α, ω-diphenyl polycarbonate of formula:

(XIII)

$$HO-\left[\underset{CH_3}{\overset{CH_3}{C}}-O-\underset{O}{\overset{\|}{C}}-O-\underset{CH_3}{\overset{CH_3}{C}}\right]_n-OH$$

in which n is an integer equal to or higher than 1 with 1-allyloxy-2,3-epoxy propane in the presence of a catalyst constituted by a tertiary amine or an alkali hydroxide.

The polycarbonates of formula XIII used as starting products for the synthesis of polyphenol derivatives according to the invention are obtained by reacting bisphenol A with COCl₂ by conventional processes. In the same way, the polysulphones of formula XIII used as starting products in the synthesis of polyphenol derivatives according to the invention can be obtained by reacting bisphenol A with dichlorodiphenylsulphone by conventional processes.

According to the fourth embodiment of the invention, the polyphenol derivative complies with the following formula:

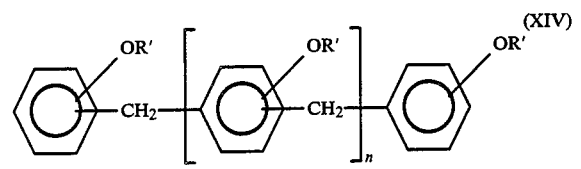

with R' representing

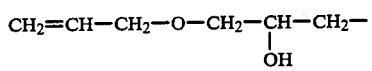

and n representing an integer equal to or higher than 1.

Such a derivative can be obtained by reacting a resol of formula:

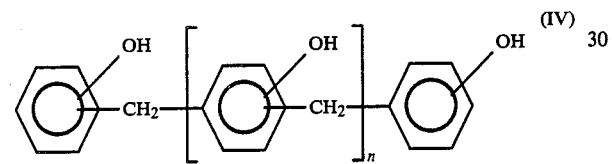

with 1-allyloxy-2,3-epoxy propane in the presence of a catalyst formed by a tertiary amine.

The resols of formula VIII used as starting products are obtained by hot reacting a phenol with a formaldehyde in the presence of an alkaline catalyst by known processes.

The polyphenol derivatives according to the invention are of considerable interest due to the simultaneous presence of two different types of reactive functions at each end of the macromolecular chain and optionally side groups, i.e. a first reactive function constituted by the allyl group and a second reactive function constituted by the secondary hydroxyl group.

Such derivatives can also be used for performing the synthesis of block copolymers and crosslinked materials by means of one or other of these two reactive functions.

It is pointed out that block copolymers are formed by alternate linkings of polymer links of different chemical natures A and B, the various possible structures being as follows: BAB, ABA, and (AB)$_n$.

Thus, with such structures, it is possible to combine the properties of two different derivatives into a single material and alternate, for example, rigid sequences with elastomer sequences. This can be obtained with the polyphenol derivatives according to the invention, on the basis of one or other of the two reactive functions present at each end of the molecule and it is then possible to use the second reactive function not used for producing the block polymer for other reactions, e.g. for crosslinking reactions.

In particular, it is possible to use the allyl function for carrying out a homopolymerization or a copolymerization with ethylenically unsaturated groups, in the presence of an adequate ion or radical catalyst.

Thus, it is possible to obtain a space lattice and the reactivity of the catalyst can be chosen in such a way that the reaction takes place at an adequately high temperature, so that below said temperature, the polymer can still be realised.

It is also possible to use the allyl function for carrying out addition reactions with other functions, e.g. with silanes

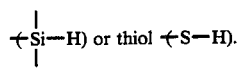

For example, the use of this reaction is of interest for preparing block copolymers of polysulphones - polysiloxanes BAB, ABA or (AB)$_n$, the polysulphone sequence A constituting the rigid phase and the polysiloxane sequence B the elastomer phase of the copolymer.

In this case, derivative B participating in the copolymerization reaction can be a polysiloxane having at its ends silane functions, e.g. alpha-omega-dihydrogen polydimethylsiloxane:

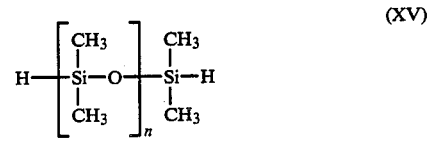

with n equal to or higher than 1.

The polycondensation reaction is as follows:

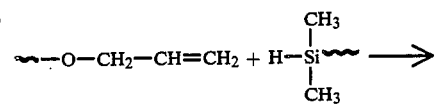

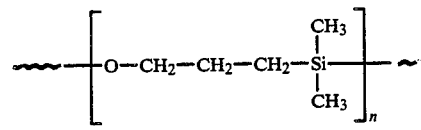

This reaction can easily be performed. Such block polymers can have a high thermal stability and a relatively low viscosity, it being possible to regulate this viscosity by using derivatives having different lengths. When these copolymers have a low viscosity, they can easily be obtained, e.g. as by injection.

According to the invention, it is possible to use the hydroxyl groups of polyphenol derivatives or the block copolymer to form a space lattice by reaction e.g. with dicarboxylic acids or derivatives of dicarboxylic diacids, such as anhydrides.

It is also possible to react the hydroxyl functions with a polyisocyanate, such as toluene diisocyanate (TDI), hexamethylene diisocyanate (HMDI) and diphenylmethane diisocyanate, according to the following reaction diagram:

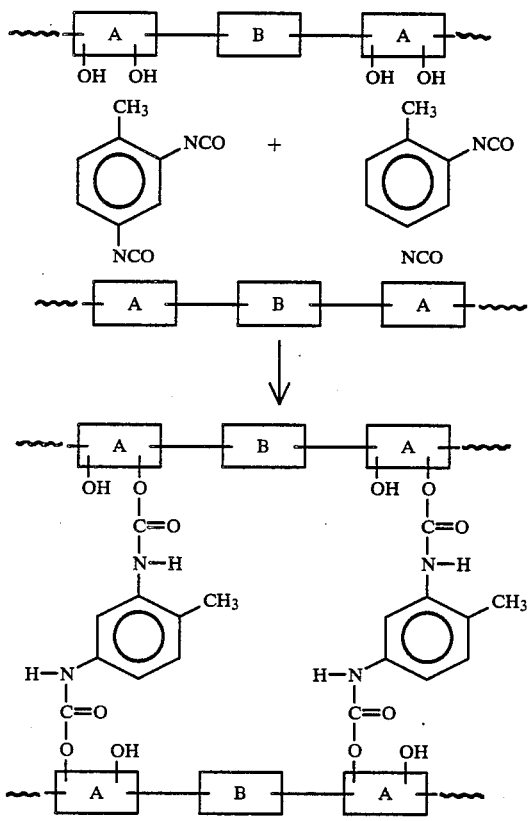

DETAILED DESCRIPTION OF THE INVENTION

Other features and advantages of the invention can be gathered from reading the following examples provided in an illustrative and non-limitative manner.

EXAMPLE 1

This example relates to the preparation of (bis-3-allyloxy-2-hydroxy-4-propanoxyphenyl)-2,2-propane, i.e. the derivative of formula VIII.

In a reactor equipped with a stirring system and a system permitting nitrogen scavenging, 228 g of bisphenol A (1 mole) and 228 g of 1-allyloxy-2,3-epoxy propane (2 moles) are mixed. The reaction mixture is then heated, solubilization of the bisphenol A in 1-allyloxy-2,3-epoxy propane taking place at about 70° to 80° C. and heating continues up to 120° C. This is followed by the introduction of 10 g of a tertiary amine constituted by N,N—dimethyldodecylamine and the temperature of 120° C. is maintained for 2 hours. This leads to 466 g of a yellowish, but transparent, viscous product (yield higher than 95%) and it is established that this product corresponds to formula VIII by chemical dosing, gel chromatography, nuclear magnetic resonance and infrared spectrometry.

EXAMPLE 2

Using the same operating procedure as in example 1, different derivatives are prepared by using in place of bisphenol A, 1,1-bis(4-hydroxyphenyl cyclohexane), 4,4'-dihydroxybenzophenone, 4,4'-dihydroxydiphenyl-sulphone, resorcinol, hydroquinone, catechol and phluoroglucinol and by nuclear magnetic resonance, infrared spectrometry and gel chromatography it is ensured that the product obtained corresponds to the reaction products of each polyphenol with 1-allyloxy-2,3-epoxy propane.

EXAMPLE 3

This example relates to the preparation of a derivative in accordance with formula X in which n is equal to 4.

In a reactor equipped with a stirring system and a system permitting nitrogen scanning is mixed 20 g of alpha, omega-diphenylpolysulphone of formula XI with $n=4$ (1/100 mole) and 23 g of 1-allyloxy-2,3-epoxy propane (0.13 mole), which corresponds to an excess. The mixture is then heated to 120° C. and the polysulphone in the allyl glycidyl ether solubilizes during the preheating period. This is followed by the addition of 0.2 g of N,N—dimethyldodecylamine and reaction is continued at 120° C. for 3 hours. The polymer obtained is purified by precipitation in hexane after dissolving in methylene chloride. In this way, the 1-allyloxy-2,3-epoxy propane and its possible homopolymer are eliminated. This leads to 20 g of a beige powder (yield above 95%) consisting of a mixture of the bifunctional oligomer of formula X in which n is equal to 4 and essentially polyfunctional oligomers having a functionality exceeding 2 resulting from the reaction of the hydroxyl functions of the polysulphone with 1-allyloxy-2,3-epoxy propane.

EXAMPLE 4

Mixing takes place in a reactor equipped with a stirring system and a nitrogen scanning system of 20 g (1/100 mole) of polysulphone according to example 3 and 2.3 g of 1-allyloxy-2,3-epoxy propane (2/100 mole) with 50 ml of chlorobenzene. The temperature is raised to 120° C. and 0.1 g of N,N—dimethyldodecylamine is added, the reaction then being continued at this temperature for 24 hours. The solvent is then eliminated under vacuum and the product obtained is dried at 80° C. and 13.5 Pa for 1 hour. The reaction yield exceeds 95% and the product obtained corresponds to the bifunction oligomer of formula X in which n is equal to 4.

EXAMPLE 5

This example relates to the preparation of an oligomer according to formula X in which n is equal to 4. In a reactor equipped with a stirring system and a nitrogen scavenging system are mixed 20 g of alpha-omega-diphenylpolysulphone of formula XI with $n=4$ (1/100 mole), 23 g of 1-allyloxy-2,3-epoxy propane and 20 g of diethylene glycol dimethyl ether (diglyme). The mixture is then heated to 120° C. and the polysulphone solubilizes in the allyl glycidyl ether - diglyme mixture during the preheating period. This is followed by the addition of 0.2 g of N,N—dimethyldodecylamine and the reaction is continued at 120° C. for 3 hours. The polymer is purified by precipitation in hexane after dissolving in methylene chloride to eliminate the diglyme excess. This leads to 20 g of a beige powder (yield above 95%) and by chemical, physicochemical and spectroscopic analysis it is ensured that it corresponds to the oligomer of formula X in which n is equal to 4.

EXAMPLE 6

This example relates to the preparation of a block polymer from the compound of formula VIII obtained in example 1 and the tetramethyldisiloxane of formula XV with n equal to 1.

456 g (1 mole) of the compound of formula VIII and 134 g (1 mole) of tetramethyldisiloxane are mixed in a reactor, equipped with a stirring system, a condenser and a nitrogen scavenging system. 1 ml of a hexachloroplatinic acid solution in tertiary butanol (1% solution) is added. The temperature is progressively raised to 70° C. The reaction mixture, which is initially opaque due to the incompatibility of the two reagents, becomes translucid after a few units of reactions. The viscosity rapidly increases and at the end of an hour, a transparent yellowish viscous product is obtained. Gel chromatography reveals a number average molecular weight of above 10,000. This polymer dissolves very rapidly in numerous organic solvents.

EXAMPLE 7

This example relates to the preparation of a block copolymer from the compound of formula VIII of example 1 and α, ω-dihydrogen polydimethylsiloxane oil of formula XV with a number average molecular weight of Mn ~1100.

45.6 g (0.1 mole) of the compound of formula VIII and 110 g (0.1 mole) of α, ω-dihydrogen polydimethylsiloxane are mixed in a reactor, equipped with a stirring system and a nitrogen scavenging system. 0.5 ml of a hexachloroplatinic acid solution in tertiary butanol (1% solution) is added. The temperature is progressively raised to 100° C. As in example 6, the reaction medium which is opaque at the start as a result of the incompatibility of the two reagents, becomes translucid after a few minutes of reaction. The viscosity rapidly increases and at the end of 1 hour a transparent, yellowish viscous product is obtained. A polymer of number average molecular weight above 20,000 is obtained, which is soluble in numerous alternate solvents.

EXAMPLE 8

This example relates to the preparation of a material crosslinked by radical polymerization of allyl double bonds from the product of formula VIII obtained in example 1. 40 g of product of formula VIII obtained in example 1 are degassed at 130° C. in an internally teflon-coated 250 ml reactor, equipped with a stirring system, a thermometer and a dropping funnel. After return to ordinary temperature, the nitrogen scavenging takes place in the reactor and 4 g of tert-butyl perbenzoate are introduced with the aid of the dropping funnel. Following homogenization, the temperature is raised to 150° C. and the stirrer is removed from the mixture during reaction. This temperature is maintained for 24 hours. This leads to a material, which is insoluble, unmeltable and has a very considerable flexibility at ordinary temperature.

EXAMPLE 9

This example relates to the preparation of a polyurethane from the product of formula VIII of example 1 by polycondensation of a diisocyanate on hydroxyl side groups of the product of formula VIII (BPADA). In a 100 ml cup, 46.5 g of BPADA (0.1 mole) are mixed with 17.4 g (0.1 mole) of toluene diisocyanate (TDI). The reaction is immediate and highly exothermic. This leads to hard, brittle thermoplastic material, whose softening point is approximately 52° C.

EXAMPLE 10

This example also relates to the preparation of a polyurethane by condensing a diisocyanate on hydroxyl side groups of BPADA (product of formula VIII). In a 100 ml cup, 40.5 g of BPADA (0.1 mole) are mixed with 25.8 g (0.1 mole) of HMDI of formula OCN—(CH$_2$)$_6$—NCO. The temperature is raised to 110° C. and during this time, the viscosity of the mixture progressively increases. A flexible thermoplastic material is obtained.

EXAMPLE 11

This example relates to the preparation of a block copolymer of poly(sulphone-seq-siloxane). In a reactor equipped with a stirring system and under nitrogen scavenging, are mixed 200 g (0.1 mole) of modified polysulphone obtained in example 5 with 110 g of polydimethylsiloxane used in example 7. 0.5 ml of a hexachloroplatinic acid solution in tertiary butanol (1% solution) is added. The temperature is progressively raised to 100° C. Homogenization of the reaction medium takes place after a few minutes and the viscosity rapidly increases. A polymer with a number average molecular weight exceeding 20,000 is obtained.

What is claimed is:

1. A block copolymer obtained by the process comprising the steps of (a) reacting a polyphenol with 1-allyloxy-2,3-epoxypropane in the presence of a basic catalyst to form a polyphenol derivative and, (b) copolymerizing said polyphenol derivative with a polysiloxane of the formula

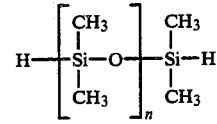

in which n is equal to or higher than 1.

2. A copolymer according to claim 1, wherein the polyphenol derivative is (bis-3-allyloxy-2-hydroxy-4-propanoxyphenyl)-2,2-propane.

3. A copolymer according to claim 1, wherein the polyphenol derivative has the formula:

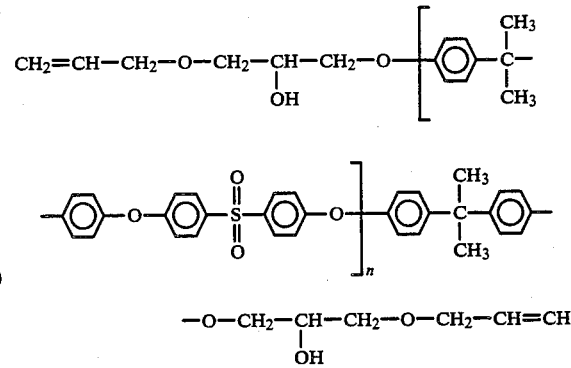

in which n is an integer equal to or higher than 1.

* * * * *